(12) United States Patent
Salemi et al.

(10) Patent No.: US 7,989,043 B2
(45) Date of Patent: Aug. 2, 2011

(54) ANTIMICROBIAL PRODUCT AND METHOD FOR USING THE SAME

(75) Inventors: Anthony S. Salemi, Des Plaines, IL (US); Anthony C. Pappageorge, Long Grove, IL (US)

(73) Assignee: Microbeguard Inc., Des Plaines, IL (US)

( * ) Notice: Subject to any disclaimer, the term of this patent is extended or adjusted under 35 U.S.C. 154(b) by 1567 days.

(21) Appl. No.: 11/352,481

(22) Filed: Feb. 10, 2006

(65) Prior Publication Data

US 2007/0190119 A1    Aug. 16, 2007

(51) Int. Cl.
*B32B 3/00*    (2006.01)
(52) U.S. Cl. ............... 428/53; D9/759; D9/761; D9/760
(58) Field of Classification Search .................... D9/739, D9/759, 760, 761, 762; 99/645
See application file for complete search history.

(56) References Cited

U.S. PATENT DOCUMENTS

| | | | |
|---|---|---|---|
| 4,081,580 A * | 3/1978 | Kato | 428/134 |
| 6,610,173 B1 * | 8/2003 | Lindsay et al. | 162/109 |
| 6,939,442 B2 | 9/2005 | Klimpl et al. | |
| 6,964,726 B2 | 11/2005 | Chen et al. | |
| 2005/0053644 A1 * | 3/2005 | Salemi et al. | 424/443 |

FOREIGN PATENT DOCUMENTS

WO    WO-2007/070649 A2 *    6/2007

* cited by examiner

*Primary Examiner* — Karlheinz R Skowronek
*Assistant Examiner* — Ali Soroush
(74) *Attorney, Agent, or Firm* — Patents & Tms, P.C.

(57) ABSTRACT

An antimicrobial product and a method for using the same display and/or store a first food product and/or a second food product. The antimicrobial product has a base layer having a first side and a second side for contacting and/or for abutting the first food product and/or the second food product. A first water resistant layer is connected to the first side of the base layer. A first antimicrobial layer is connected to the first water resistant layer. A second water resistant layer is connected to the second side of the base layer. The base layer and/or the first water resistant layer is colored and/or displays a first color and/or a second color. The second water resistant layer and/or the first antimicrobial layer is transparent to expose and/or to display the first color of the base layer and/or the second color of the first water resistant layer. A second antimicrobial layer is connected to the second water resistant layer. The antimicrobial product is formed with a texture having first depressions and/or second depressions for contacting and/or for abutting the first food product and/or the second food product. The first color of the base layer and/or the second color of the first water resistant layer enhances and/or improves a color and/or an appearance of the first food product and/or the second food product.

20 Claims, 2 Drawing Sheets

ANTIMICROBIAL PRODUCT AND METHOD FOR USING THE SAME

BACKGROUND OF THE INVENTION

The present invention generally relates to an antimicrobial product and a method for using the same. More specifically, the present invention relates to an antimicrobial product and a method for using the same with a food product or food products. The product may be a single-sided antimicrobial product or a double-sided antimicrobial product. The single-sided antimicrobial product may have a base layer having a first side and a second side. A first water resistant layer may be attached to and/or may cover the first side of the base layer. A first antimicrobial layer and/or a first coating which contains an antimicrobial material may be attached to and/or may cover the first water resistant layer of the single-sided antimicrobial product. The base layer and/or the first water resistant layer may have a first color and/or a second color, respectively. A second water resistant layer may be attached to and/or may cover the second side of the base layer. The second water resistant layer, the first antimicrobial layer and/or the first coating may be transparent to expose and/or to display the first color of the base layer and/or the second color of the first water resistant layer. Moreover, the single-sided antimicrobial product may be formed and/or may provide a texture having first depressions and/or second depressions for contacting, for abutting, for covering, for packaging and/or for wrapping the food product or the food products.

In another embodiment, a second antimicrobial layer and/or a second coating which may contain the antimicrobial material may be attached to and/or may cover the second water resistant layer of the single-sided antimicrobial product. As a result, the double-sided antimicrobial product may be formed via the second antimicrobial layer and/or the second coating and the single-sided antimicrobial product. The second antimicrobial layer and/or the second coating may be transparent to expose and/or to display the first color of the base layer. Further, the double-sided antimicrobial product may be formed to provide the texture having the first depressions and/or the second depressions for stacking, for separating, for packaging, for wrapping and/or for displaying the food products. Moreover, the first color and/or the second color may enhance and/or may improve a color and/or an appearance of the food product and/or food products.

It is generally known to provide a paper sheet to display and/or to package food products in a retail food industry. The paper sheet is inserted between each of the food products to separate isolate the food products from each other. Further, the paper sheet is inserted and/or is placed between the food products and a holding tray for displaying the food products in a retail food establishment. Moreover, the food products may be covered by, may be packaged by and/or may be wrapped with the paper sheet for storing, for shipping, for transporting, and/or for packaging the food products. Additionally, the paper sheet may protect the food products from bacteria, from molds and/or from mildew which may contaminate the food products during displaying and/or storing the food products at the retail food establishment.

Traditionally, the paper sheet is constructed from a paper pulp and an additive to increase and/or to maintain a paper strength of the paper sheet for displaying and/or for packaging the food products. The paper pulp has a color which may correspond to a type of food products which is being displayed and/or packaged with the paper sheet. For example, seafood products may be displayed on and/or may be packaged with a paper sheet which is colored white. The color of the paper sheet may be, for example, peach, green, white or pink. The color of the paper sheet enhances and/or improves a color and/or an appearance of the food products for displaying and/or for packaging the food products for sale at the retail food establishment.

However, the paper sheet may be destroyed by and/or may be damaged by juices, moisture and/or fluids which may dissipate from the food products during display at the retail food establishment. As a result, the food sheet is incapable of preventing contamination of the food products from bacteria, molds and/or mildew during displaying and/or packaging of the food products for sale at the retail food establishments. Further, bacteria, molds and/or mildew may penetrate and/or may contaminate the food products because the paper sheet did not surround, did not enclose and/or did not seal the food products from the bacteria, the molds and/or the mildew. Still further, the color of the paper sheet may not enhance the color of and/or the appearance of more than one type of food products for displaying the food products for sale at the retail food establishment. As a result, the paper sheet may not be used to display more than one type of food products for sale at the retail food establishment.

A need, therefore, exists for an antimicrobial product and a method for using the same which may prevent contamination of food products from micro-organisms, bacteria, molds, mildew and/or microbes for displaying, for storing and/or for packaging a food product and/or food products. Further, a need exists for an antimicrobial product and a method for using the same which may have a first antimicrobial layer and/or a second antimicrobial layer to prevent contamination of a food product and/or food products from micro-organisms, bacteria, molds, mildew and/or microbe. Still further, a need exists for an antimicrobial product and a method for using the same which may have a first water resistant layer and/or a second water resistant layer to prevent damage and/or to prevent destruction of a paper layer from juices, from moisture and/or from fluids of a food product and/or food products. Moreover, a need exists for an antimicrobial product and a method for using the same which may have a first color displayed on a first side and/or a second color displayed on a second side to enhance a color of a food product and/or food products displayed thereon. Furthermore, a need exists for an antimicrobial product and a method for using the same which may be formed to provide a texture having first depressions and/or second depressions for contacting and/or for abutting a food product and/or food products.

SUMMARY OF THE INVENTION

The present invention generally relates to an antimicrobial product and a method for using the same. Further, the antimicrobial product may be a single-sided antimicrobial product and/or a double-sided antimicrobial product. The antimicrobial product may have a base layer having a first side and/or a second side. A first water resistant layer may attached to, may be adhered to and/or may cover the first side of the base layer. A first antimicrobial layer may be attached to, may be adhered to and/or may cover the first water resistant layer. A second water resistant layer may be attached to, may be adhered to and/or may cover the second side of the base layer. A second antimicrobial layer may be attached to, may be adhered to and/or may cover the second water resistant layer. The base layer and/or the first water resistant layer may be colored and/or may display a first color and/or a second color, respectively. The first antimicrobial layer, the second water resistant layer and/or the second antimicrobial layer may be transparent and/or the like. As a result, the first color and/or"

the second color of the base layer and/or the first water resistant layer, respectively, may be exposed and/or may be displayed via the first antimicrobial layer, the second water resistant layer and/or the second antimicrobial layer. The antimicrobial product may be formed to provide a texture having first depressions and/or second depressions for contacting, for abutting, for displaying, for wrapping and/or for packaging the first food product and/or the second food product.

To this end, in an embodiment of the present invention, an antimicrobial product for preventing contamination of a first food product or a second food product by a micro-organism wherein the first food product has a first color wherein the second food product has a second color is provided. The antimicrobial product has a base layer defined by a length and a width wherein the base layer has a top side and a bottom side wherein the bottom side is located opposite to the top side and further wherein the base layer forms a plane. Further, the antimicrobial product has a first antimicrobial layer connected to the top side of the base layer wherein the first antimicrobial layer covers the top side of the base layer. Still further, the antimicrobial product has a second antimicrobial layer connected to the bottom side of the base layer wherein the second antimicrobial layer covers the bottom side of the base layer wherein the first antimicrobial layer or the second antimicrobial layer prevents migration of the micro-organism across the plane of the base layer. Moreover, the antimicrobial product has a plurality of depressions formed in the base layer, the first antimicrobial layer and the second antimicrobial layer wherein the plurality of depressions are uniform and are continuous on the base layer wherein the first antimicrobial layer or the second antimicrobial layer prevents the micro-organism from contaminating the first food product.

In an embodiment, the antimicrobial product has a water resistant layer attached to the base layer wherein the water resistant layer is located between the base layer and the first antimicrobial layer.

In an embodiment, the antimicrobial product has a water resistant layer attached to the base layer wherein the water resistant layer is located between the base layer and the second antimicrobial layer.

In an embodiment, the antimicrobial product has a color associated with the top side of the base layer wherein the color corresponds to the first color of the first food product.

In an embodiment, the antimicrobial product has a color associated with the bottom side of the base layer wherein the color corresponds to the second color of the second food product.

In an embodiment, the base layer is made from a paper pulp.

In an embodiment, the first food product is adjacent to the first antimicrobial layer and the second food product is adjacent to the second antimicrobial layer.

In another embodiment, an antimicrobial product for preventing contamination of a first food product or a second food product from a micro-organism wherein the first food product has a first color wherein the second food product has a second color is provided. The antimicrobial product has a base layer defined by a length and a width wherein the base layer has a top side and a bottom side wherein the bottom side is opposite to the top side and further wherein the base layer forms a plane wherein a first color is associated with the bottom side of the base layer wherein a second color is associated with the top side of the base layer wherein the first color of the bottom side corresponds to the first color of the food product wherein the second color of the top side corresponds to the second color of second food product. Further, the antimicrobial product has a first antimicrobial layer connected to the top side of the base layer wherein the first antimicrobial layer covers the top side of the base layer wherein the first antimicrobial layer prevents the micro-organism from contaminating the first food product or the second food product.

In an embodiment, the antimicrobial product has a water resistant layer attached to the base layer wherein the water resistant layer is located between the first antimicrobial layer and the base layer.

In an embodiment, the antimicrobial product has a second antimicrobial layer is connected to the bottom side of the base layer wherein the second antimicrobial layer prevents the micro-organism from contaminating the first food product or the second food product.

In an embodiment, the antimicrobial product has a water resistant layer attached to the bottom side of the base layer wherein the water resistant layer is transparent.

In an embodiment, the antimicrobial product has

In an embodiment, the base layer is made from a paper pulp.

In an embodiment, the antimicrobial product has a plurality of depressions formed in the base layer and the first antimicrobial layer wherein the plurality of depressions.

In another embodiment, a method for using an antimicrobial product to prevent contamination of a first food product or a second food product by a micro-organism wherein first food product has a first color wherein the second food product has a second color is provided. The method has the step of providing an antimicrobial product having a base layer defined by a length and a width wherein the base layer has a top side and a bottom side wherein the bottom side is located opposite to the top side and further wherein the base layer has a first color wherein a water resistant layer is attached to the top side of the base layer wherein the water resistant layer has a second color wherein the first color is a different color than the second color wherein a first antimicrobial layer is attached to the water resistant layer wherein the first antimicrobial layer prevents the micro-organism from contaminating the first food product or the second food product. Moreover, the method has the step of forming a texture on the antimicrobial product wherein the texture has a plurality of depressions.

In an embodiment, the method has the step of positioning the first food product on the antimicrobial product wherein the first food product is adjacent to the first color of the base layer wherein the first color of the base layer corresponds to the first color of the first food product.

In an embodiment, the method has the step of positioning the second food product on the antimicrobial product wherein the second food product is adjacent to the second color of the water resistant layer wherein the second color of the water resistant layer corresponds to the second color of the second food product.

In an embodiment, the method has the step of enclosing the first food product or the second food product with the antimicrobial product wherein the antimicrobial product prevents the micro-organism from contaminating the first food product or the second food product.

In an embodiment, the method has the step of inserting the antimicrobial product between the first food product and the second food product wherein the first color is adjacent to the first food product.

In an embodiment, the method has the step of providing air flow to the first food product or the second food product via the texture of the antimicrobial product.

In an embodiment, the method has the step of connecting a second antimicrobial layer to the bottom side of the base layer of the antimicrobial product wherein the second antimicrobial layer prevents the micro-organism from contaminating the first food product or the second food product.

It is, therefore, an advantage of the present invention to provide an antimicrobial product and a method for using the same.

Another advantage of the present invention is to provide an antimicrobial product and a method for using the same which may have one or more antimicrobial layers to prevent contamination of a food product from bacteria, molds, mildew, micro-organisms and/or microbes.

And, another advantage of the present invention is to provide an antimicrobial product and a method for using the same which may have one or more water resistant layers to prevent damage and/or to prevent destruction of the antimicrobial product from juice, moisture and/or fluids of a food product.

Yet another advantage of the present invention is to provide an antimicrobial product and a method for using the same which may have a first color on a first side and/or a second color on a second side corresponding to a first food product and/or a second food product, respectively.

A further advantage of the present invention is to provide an antimicrobial product and a method for using the same which may be colored and/or may display a first color to enhance and/or to improve a color and/or an appearance of a food product displayed adjacent to the first color.

A still further advantage of the present invention is to provide an antimicrobial product and a method for using the same which may have indicia corresponding to a food product, a retail food establishment, a corporate entity and/or the like.

Moreover, an advantage of the present invention is to provide an antimicrobial product and a method for using the same which may be formed to provide a texture having first depressions and/or second depressions for displaying, for packaging, for contacting and/or for abutting a first food product and/or a second food product.

And, another advantage of the present invention is to provide an antimicrobial product and a method for using the same which may be formed to provide a texture having first depressions and/or second depressions for increasing air flow to a food product for preventing contamination of the food product from bacteria, molds, mildew, micro-organisms and/or microbes.

Yet another advantage of the present invention is to provide an antimicrobial product and a method for using the same which may be inserted between a first food product and a second food product to provide an antimicrobial layer adjacent to the first food product and/or the second food product.

Another advantage of the present invention is to provide an antimicrobial product and a method for using the same which may be inserted between a first food product and a second food product to prevent adhesion to the first food product and/or to the second food product.

Yet another advantage of the present invention is to provide an antimicrobial product and a method for using the same which may provide a moisture barrier between a food product and ice and/or water.

A still further advantage of the present invention is to provide an antimicrobial product and a method for using the same which may prevent a liquid pooling around a first food product and/or a second food product.

Moreover, an advantage of the present invention is to provide an antimicrobial product and a method for using the same which may not absorb moisture to prevent and/or to delay drying and/or decaying of a food product.

And, another advantage of the present invention is to provide an antimicrobial product and a method for using the same which may increase and/or may preserve a shelf life of one or more food products.

Yet another advantage of the present invention is to provide an antimicrobial product and a method for using the same which may display indicia to provide instructions of use to a user.

A further advantage of the present invention is to provide an antimicrobial product and a method for using the same which may be used to stack more than one food product in a container and/or in a bin or on a tray and/or on a pan.

A still further advantage of the present invention is to provide an antimicrobial product and a method for using the same which may provide an interleaf between a first food product and a second food product.

Moreover, an advantage of the present invention is to provide an antimicrobial product and a method for using the same which may provide a wrapping and/or a packaging for a food product.

And, another advantage of the present invention is to provide an antimicrobial product and a method for using the same which may provide a sanitary liner and/or a sanitary cover for a food product and/or a display unit.

Yet another advantage of the present invention is to provide an antimicrobial product and a method for using the same which may provide a first color on a base layer and a second color on a water resistant layer corresponding to a first food product and a second food product, respectively.

A further advantage of the present invention is to provide an antimicrobial product and a method for using the same which may provide a silver zeolite within or on a layer for preventing contamination of a food product by micro-organisms, bacteria, molds, mildew and/or microbes.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally relates to an antimicrobial product and a method for using the same. More specifically, the present invention relates to an antimicrobial product and a method for using the same which may be used with a first food product and/or with a second food product. The antimicrobial product may have a base layer having a first side and a second side for contacting and/or for abutting the first food product and/or the second food product. A first water resistant layer may be attached to, may be adhered to and/or may cover the first side of the base layer. A first antimicrobial layer may be attached to, may be adhered to and/or may cover the first water resistant layer. A second water resistant layer may be attached to, may be adhered to and/or may cover the second side of the base layer.

The base layer and/or the first water resistant layer may be colored and/or may display a first color and/or a second color, respectively. The second water resistant layer and/or the first antimicrobial layer may be transparent to expose and/or to display the first color of the base layer and/or the second color of the first water resistant layer, respectively. In an embodiment, the antimicrobial product may have a second antimicrobial layer which may be attached to, may be adhered to and/or may cover the second water resistant layer. The antimicrobial product may be indented to form a texture for contacting and/or for abutting the first food product and/or the second food product.

Figure 1:
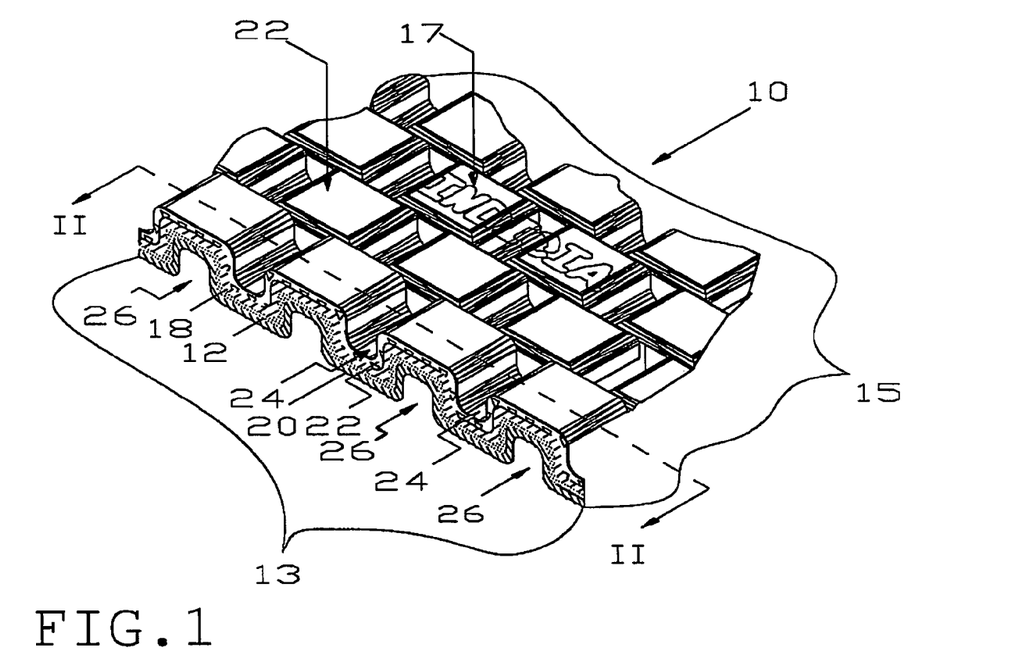
FIG. 1 illustrates a perspective view of an antimicrobial product in an embodiment of the present invention.
Figure 2:
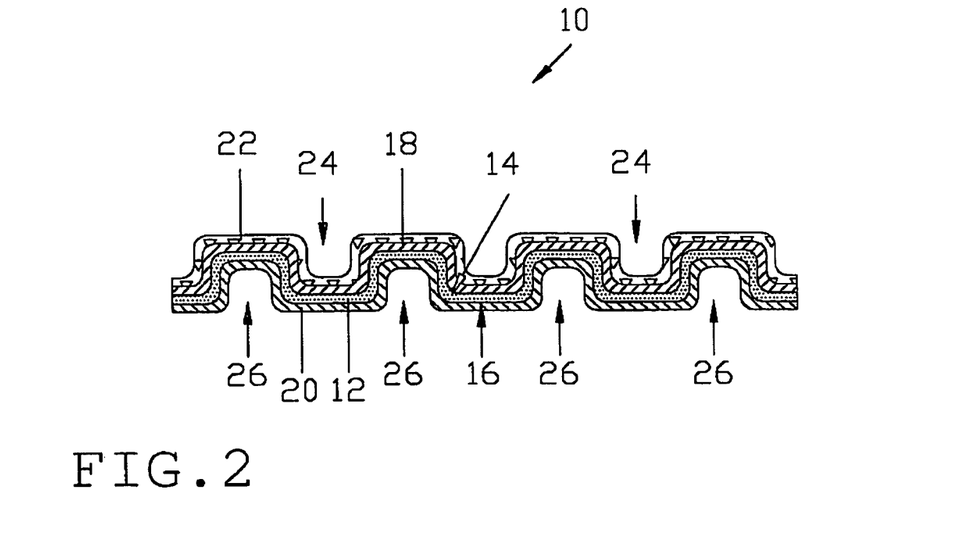
FIG. 2 illustrates a cross-sectional view taken generally along line II-II of the antimicrobial product of FIG. 1 in an embodiment of the present invention.
Figure 3:
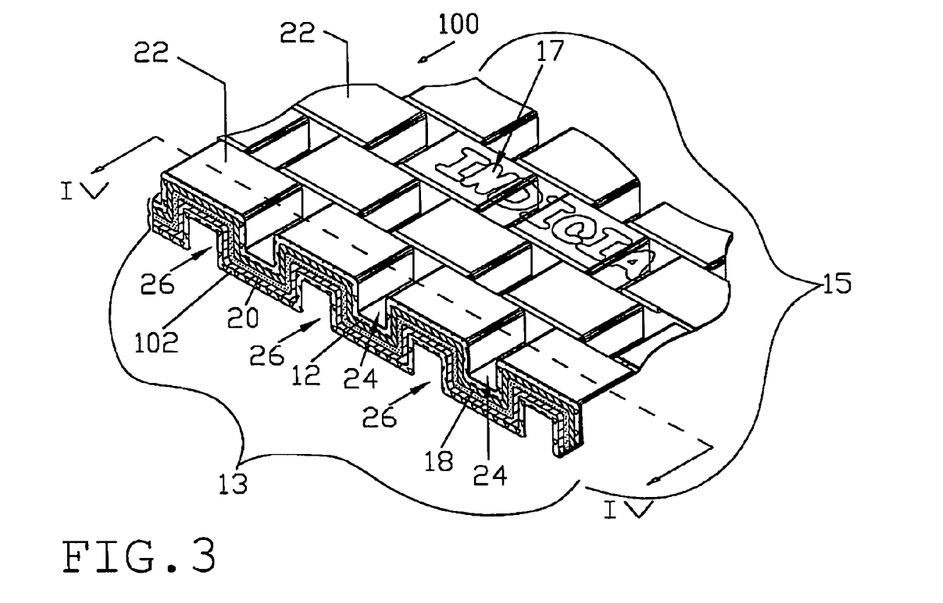
FIG. 3 illustrates a perspective view of an antimicrobial product in an embodiment of the present invention.
Figure 4:
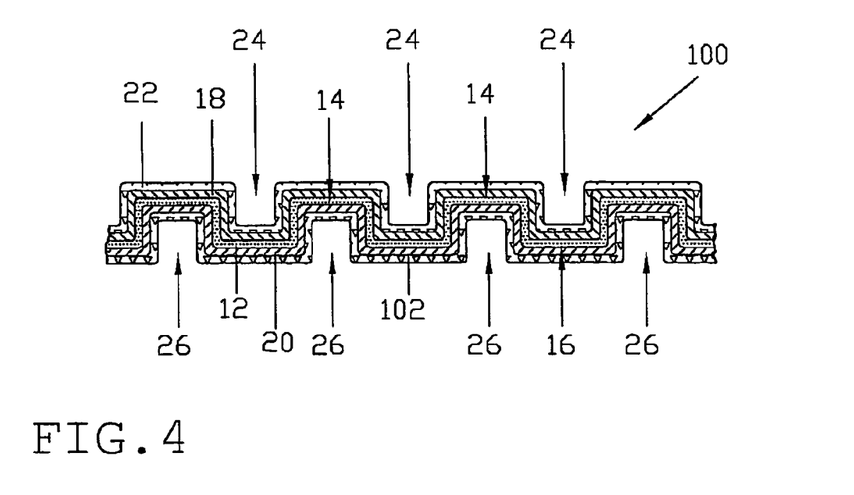
FIG. 4 illustrates a cross-sectional view taken generally along line IV-IV of the antimicrobial product of FIG. 3 in an embodiment of the present invention.

Referring now to the drawings wherein like numerals refer to like parts, FIGS. 1 and 3 illustrate an antimicrobial product 10 and an antimicrobial product 100, respectively, in embodiments of the present invention. The antimicrobial product 10 may be, for example, a single-sided antimicrobial product as shown in FIGS. 1 and 2. The antimicrobial product 100 may be, for example, a double-sided antimicrobial product as shown in FIGS. 3 and 4. The antimicrobial product 10 and/or the antimicrobial product 100 (hereinafter "the antimicrobial products 10, 100") may be placed on a surface (not shown in the figures) of a display unit, such as, for example, a pan, a tray, a bin, a rack, a cart and/or the like. The surface may have a micro-organism (not shown in the figures), such as, for example, bacteria, microbes, fungus, mold spores, mildew and/or the like.

The antimicrobial products 10, 100 may be inserted between a first food product (not shown in the figures) and a second food product (not shown in the figures). The antimicrobial products 10, 100 may be covered, may be wrapped around, may be in contact and/or may be surrounding the first food product and/or the second food product. The first food product and/or the second food product may be a perishable, such as, for example, beef, seafood, poultry, pork, fish, a vegetable, a fruit, a bread, a pastry, a raw dough and/or the like. It should be understood that the perishable may be any food which may spoil and/or may decay as known to one of ordinary skill in the art.

The antimicrobial products 10, 100 may have a length 13 and a width 15 as shown in FIGS. 1 and 3, respectively. Still further, the length 13 and the width 15 may be, for example, twelve inches by eighteen inches, twenty-four inches by twenty-four inches, thirty-six inches by twenty-four inches and/or the like. The antimicrobial products 10, 100 may be sized to be insertable into and/or onto the surface of the display unit. The antimicrobial products 10, 100 may have a perimeter having a shape which may be any shape, such as, for example, a square, a rectangle, a circle, an oval, a triangle, an eclipse, a hexagon and/or the like. The present invention should not be limited to a specific embodiment of a shape of the antimicrobial products 10, 100.

Moreover, the antimicrobial products 10, 100 may have a base layer 12 having a top side 14 and a bottom side 16. The top side 14 is located opposite to the bottom side 16 of the base layer 12. The base layer 12 may be made from a paper, such as, for example, a recycled kraft paper, a virgin kraft paper, a grey bogus paper, a news print paper, a butcher paper, a bleached kraft paper and/or the like. The paper of the base layer 12 may have a weight range between, for example, fifteen pounds and ninety pounds. The base layer 12 may be colored and/or may display a first color, such as, for example, white and/or cream. The present invention should not be deemed as limited to a specific embodiment of the first color of the base layer 12.

An adhesive (not shown in the figures) may be located on and/or may cover the top side 14 and/or the bottom side 16 of the base layer 12. A first water resistant layer 18 may be connected to, may be attached to, may be formed on and/or may cover the top side 14 of the base layer 12 as shown in FIGS. 1-4. The first water resistant layer 18 may be adhered to the top side 14 of the base layer 12 via the adhesive for connecting the first water resistant layer 18 to the base layer 12. A second water resistant layer 20 may be connected to, may be attached to, may be formed on and/or may cover the bottom side 16 of the base layer 12. The second water resistant layer 20 may be adhered to the bottom side 16 of the base layer 12 via the adhesive for connecting the second water resistant layer 20 to the base layer 12. The first water resistant layer 18 and/or the second water resistant layer 20 may be made from, for example, a polyethylene, a polyurethane and/or the like. The first water resistant layer 18 may be colored and/or may display a second color, such as, black, peach, green, black, white and/or pink. The first color of the base layer 12 may be a different color than the second color of the first water resistant layer 18. The present invention should not be deemed as limited to a specific embodiment of the second color of the first water resistant layer 18.

The second water resistant layer 20 may be transparent and/or the like. The bottom side 16 of the base layer 12 may be viewed through the second water resistant layer 18. As a result, the first color of the base layer 12 may be exposed, may be displayed and/or may be viewable via the second resistant layer 18. The first color of the base layer 12 may correspond to, may be associated with and/or may be based on a color of the first food product.

In an embodiment, the first color of the base layer 12 may be black and the first food product may be beef and/or pork with a redish color. The black color of the base layer 12 may contrast the redish color of the first food product and may make the redish color of the first food product appear to be more colorful. As a result, the first food product may appear to be fresher when displayed adjacent to the first color of the base layer 12. In another embodiment, the first color of the base layer 12 may be white and the first food product may be seafood with a whitish color. The white color of the base layer may compliment the whitish color of the first food product and may make the whitish color of the first food product appear to be less colorful. As a result, the first food product may appear to be fresher when displayed adjacent to the first color of the base layer 12.

The first water resistant layer 18 and/or the second water resistant layer 20 may be coated with and/or may be cover with the adhesive. A first antimicrobial layer 22 may be connected to, may be attached to, may be formed on and/or may cover the first water resistant layer 18 as shown in FIGS. 1-4. The first antimicrobial layer 22 may be adhered to the first water resistant layer 18 via the adhesive for connecting the first antimicrobial layer 22 to the base layer 12. A second antimicrobial layer 102 may be connected to, may be attached to, may be formed on and/or may cover the second water resistant layer 20 as shown in FIGS. 3 and 4. The second antimicrobial layer 102 may be adhered to the second water resistant layer 20 via the adhesive for connecting the second antimicrobial layer 102 to the base layer 12. The first antimicrobial layer 22 and/or the second antimicrobial layer 102 may prevent and/or may delay growth and/or migration of the micro-organism.

The first antimicrobial layer 22 and/or the second antimicrobial layer 102 may contain an active antimicrobial ingredient, such as, for example, silver zeolite. The first antimicrobial layer 22 and/or the second antimicrobial layer 102 may be, for example, a polyethylene covered with the active antimicrobial ingredient. The first antimicrobial layer 22 and/or the second antimicrobial layer 102 may be a coating solution containing the active antimicrobial ingredient.

Further, the first antimicrobial layer 22 and/or the second antimicrobial layer 102 may be a substrate, such as, for example, a polyethylene, a polyurethane and/or the like which may contain the active antimicrobial ingredient. The active antimicrobial ingredient may have a concentration by weight in a range between, for example, one percent and ten percent of the first antimicrobial layer 22 and/or the second antimicrobial layer 102. It should be understood that substrate may be any substrate which may be capable of containing the active antimicrobial ingredient as known to one of ordinary skill in the art.

The first antimicrobial layer 22 and/or the second antimicrobial layer 102 may be transparent and/or the like. The first water resistant layer 18 may be viewable through the first antimicrobial layer 22. As a result, the second color of the first water resistant layer 18 may be exposed, may be displayed and/or may be viewable via the first antimicrobial layer 22. The second color of the first water resistant layer 18 may correspond to, may be associated with and/or may be based on a color of the second food product. The bottom side 16 of the base layer 12 may be viewable through the second antimicrobial layer 102. As a result, the first color of the base layer 12 may be exposed, may be displayed and/or may be viewable via the second water resistant layer 20 and/or the second antimicrobial layer 102.

In an embodiment, the second color of the first water resistant layer 18 may be black and the second food product may be beef and/or pork with a redish color. The black color of the first water resistant layer 18 may contrast the redish color of the second food product and may make the redish color of the second food product appear to be more colorful. As a result, the second food product may appear to be fresher when displayed adjacent to the second color of the first water resistant layer 18. In another embodiment, the second color of the first water resistant layer 18 may be white and the second food product may be seafood with a whitish color. The white color of the first water resistant layer 18 may compliment the whitish color of the second food product and may make the whitish color of the second food product appear to be less colorful. As a result, the second food product may appear to be fresher when displayed adjacent to the second color of the first water resistant layer 18.

Furthermore, indicia 18 may be applied to, may be displayed and/or may be printed onto the top side 14 and/or the bottom side 16 of the base layer 12 of the antimicrobial products 10, 100 as shown in FIGS. 1 and 3. The indicia 18 may relate to, for example, an entity, such as, for example, corporate entity, a retail food establishment, a manufacturer of the antimicrobial products 10, 100 and/or the like. The indicia 18 may be associated with, may correspond to, may be based on and/or may identify the first food product and/or the second food product. The indicia 18 may provide instructions to a user for using, for storing and/or for discarding the antimicrobial products 10, 100. The indicia 18 may be applied to the base layer 16 by a printing device, such as, for example, a web printing press, a printing screen, a computer printer, a laser printer and/or the like. The present invention should not be limited to a specific embodiment of the entity of the indicia 18. It should be understood that the printing device may be any printing device as known to one of ordinary skill in the art.

As further illustrated in FIGS. 1-4, the antimicrobial products 10, 100 may be textured and/or may be indented to form first depressions 24 and/or second depressions 26. The first depressions 24 and the second depressions 26 may alternate across the length 13 and/or the width 15 of the antimicrobial products 10, 100. The first depressions 24 and/or the second depressions 26 may have a shape, such as, for example, a square, a triangle, a circle, a rectangle, a pentagon, an octagon and/or the like. It should be understood that the shape of the first depressions 24 and/or of the second depressions 26 may be any shape as known to one of ordinary skill in the art. The first depressions 24 and/or the second depressions 26 may form and/or may provide a texture on and/or to the antimicrobial products 10, 100.

Furthermore, the antimicrobial products 10, 100 may be placed on, may be located on and/or may be used with the surface of the display unit as, for example a liner and/or as a cover for the display unit. The second water resistant layer 18 of the antimicrobial product 10 may adjacent to, may contact, may abut and/or may cover the surface of the display unit. The second antimicrobial layer 102 of the antimicrobial product 100 may be adjacent to, may contact may abut and/or may cover the surface of the display unit. The second food product may be placed on, may be adjacent to, may be displayed on, may contact and/or may abut the first antimicrobial layer 22 of the antimicrobial products 10, 100. The first antimicrobial layer 20, the first water resistant layer 18, the base layer 12 and/or the second water resistant layer 20 of the antimicrobial products 10, 100 may be located between and/or may be positioned between the surface of the display unit and the second food product. The first antimicrobial layer 22, the first water resistant layer 18, the base layer 12, the second water resistant layer 20 and/or the second antimicrobial layer 102 of the antimicrobial product 100 may be located between and/or may be positioned between the second food product and the surface of the display unit.

The antimicrobial products 10, 100 may prevent growth and/or migration of the micro-organism from the surface of the display unit to and/or between the second food product. As a result, the first antimicrobial layer 22 and/or the second antimicrobial layer 102 of the antimicrobial products 10, 100 may prevent and/or may delay contamination of the second food product by the micro-organism. The second food product may be displayed on and/or may be stored on the display unit and/or on the products 10, 100. The second color of the first water resistant layer 18 may be displayed adjacent to and/or may be exposed adjacent to the second food product via the first antimicrobial layer 22.

The second color of first water resistant layer 18 may appear to increase or to decrease a colorfulness of the second food product. In an embodiment, the second color of the first water resistant layer 18 may be, for example, black and the second food product may be beef or pork with the redish color. The redish color of the beef or the pork may appear to be enhanced and/or to be improved by displaying the beef or the pork adjacent to the second color of the first water resistant layer 18. In another embodiment, the second color of the first water resistant layer 18 may be, for example, green and the second food product may be a vegetable with a greenish color. The greenish color of the vegetable may appear to be enhanced and/or to be improved by displaying the vegetable adjacent to the second color of the first water resistant layer 18.

Alternatively, the first antimicrobial layer 22 of the antimicrobial products 10, 100 may be adjacent to, may contact, may cover and/or may abut the surface of the display unit for exposing the second water resistant layer 20 and/or the second antimicrobial layer 102, respectively. The first food product may be placed on, may contact, may abut and/or may be displayed on the second water resistant layer 20 and/or the second antimicrobial layer 102 of the antimicrobial products 10, 100, respectively. As a result, the second antimicrobial layer 102, the second water resistant layer 20, the base layer 12, the first water resistant layer 18 and/or the first antimicrobial layer 22 may be positioned between and/or may be located between the first food product and the surface of the display unit. The first antimicrobial layer 22 and/or the second antimicrobial layer 102 may prevent the micro-organism from contaminating the first food product on the antimicrobial products 10, 100. The first antimicrobial layer 22 and/or the second antimicrobial layer may prevent and/or may delay migration of the micro-organism from the display unit to the first food product on the antimicrobial products 10, 100. As a result, a shelf life of the first food product and/or of the second food product may be increased via the first antimicrobial layer 22 and/or the second antimicrobial layer 102.

The first food product may be displayed adjacent to the first color of the base layer 12 via the second water resistant layer 20 and/or the second antimicrobial layer 102. The first color of the base layer 12 may increase or may decrease a colorfulness of the first food product being displayed adjacent to the first color of the base layer 12. In an embodiment, the first color of the base layer 12 may be, for example, white, and the first food product may be seafood with a whitish color. The whitish color of the seafood may appear to be enhanced and/or to be improved by displaying the seafood adjacent to the first color of the base layer 12. In another embodiment, the first color of the base layer 12 may be, for example, pink, and the first food product may be a fish with a pinkish color. The pinkish color of the fish may appear to be enhanced and/or to be improved by displaying the fish adjacent to the first color of the base layer 12.

The texture, the first depressions 24 and/or the second depressions 26 of the antimicrobial products 10, 100 may permit, may provide and/or may allow airflow and/or air pockets between the first food product, the second food product and the antimicrobial products 10, 100. The airflow and/or the air pockets between the antimicrobial products 10, 100 and the first food product and/or the second food product may prevent and/or delay growth and migration of the micro-organism to the first food product and/or the second food product. The antimicrobial products 10, 100 may form and/or may provide, for example, a cover for the first food product and/or the second food product which may be displayed, be shipped, be transported and/or be stored on the display unit. The texture, the first depressions 24 and/or the second depressions 26 of the antimicrobial products 10, 100 may prevent and/or may delay the micro-organism from contaminating the first food product and/or the second food product. As a result, the shelf life of the first food product and/or the second food product may be increased via the texture, the first depressions 24 and/or the second depressions of the antimicrobial products 10, 100.

The first food product, the second food product and/or the antimicrobial products 10, 100 may be displayed on and/or may be stored over ice to maintain the first food product and/or the second food product at a low temperature. The airflow and/or the air pockets from the texture, the first depressions 24 and/or the second depressions 26 of the antimicrobial products 10, 100 may provide assistance for maintaining the first food product and/or the second food product at the low temperature to preserve the first food product and/or the second food product. The antimicrobial products 10, 100 may form and/or may provide a moisture barrier between the ice and the first food product and/or the second food product. As a result, the low temperature may increase the shelf life of the first food product and/or the second food product.

The first water resistant layer 18 and/or the second water resistant layer 20 may form and/or may provide, for example, a moisture barrier between the first food product, the second food product, the display unit and/or the antimicrobial products 10, 100. The first water resistant layer 18 and/or the second water resistant layer 20 may not absorb moisture, fluids and/or juices from the first food product and/or the second food product. The first water resistant layer 18 and/or the second water resistant layer 20 may form and/or may provide, for example, a sanitary barrier between the first food product, the second food product, the display unit, the micro-organism and/or the antimicrobial products 10, 100. As a result, the first water resistant layer 18 and/or the second water resistant layer 20 may prevent and/or may delay contamination of the first food product and/or the second food product by the micro-organism. The first water resistant layer 18 and/or the second water resistant layer 20 may prevent and/or may delay decaying and/or drying of the first food product and/or the second food product. As a result, the first water resistant layer 18 and/or the second water resistant layer 20 may increase the shelf life of the first food product and/or the second food product.

The first water resistant layer 18 and/or the second water resistant layer 20 may prevent the moisture, the fluids and/or the juices of the first food product and/or of the second food product from contacting and/or from permeating the antimicrobial products 10, 100. The first water resistant layer 18 and/or the second resistant layer 20 may prevent the moisture, the fluids and/or the juices from destroying, from damaging and/or from harming the base layer 12 of the antimicrobial products 10, 100. The first water resistant layer 18 may prevent the first food product and/or the second food product from adhering to and/or from sticking to the antimicrobial products 10, 100.

The first food product and/or the second food product may be stacked on top of and/or may be placed on top of one or more first food products and/or one or more second food products. As a result, one or more first food products and/or one or more second food products may be displayed, may be stored, may be wrapped and/or may be packaged. The antimicrobial products 10, 100 may be inserted between, may be located between and/or may be positioned between one or more first food products and/or one or more second food products. As a result, the antimicrobial products 10, 100 may form and/or may provide, for example, an interleaf between one or more first food products, one or more second food products and/or the display unit.

One or more first food products and/or one or more second food products may be stacked and/or may be stored inside an interior of a storage container (not shown in the figures), such as, for example, a bin, a pan, a canister and/or the like. The antimicrobial products 10, 100 may be inserted between, may be located between and/or may be positioned between one or more first food products and/or one or more second food products inside the interior of the storage container. The antimicrobial products 10, 100 may form and/or may provide, for example, the interleaf between one or more first food products and/or one or more second food products inside the interior of the storage container. The antimicrobial products 10, 100 may separate one or more first products and/or one or more second products which may be stacked and/or may be stored in the storage container. The first water resistant layer 18 and/or the second water resistant layer 20 may prevent and/or may delay growth and/or migration of the micro-organism to, from and/or between the one or more first food products, one or more second food products, the display unit and/or the storage container. It should be understood that the storage container may be any storage container which may be capable of receiving and/or of storing one or more first food products and/or one or more second food products.

One or more first food products and/or one or more second food products may be wrapped and/or may be packaged with the antimicrobial products 10, 100. The antimicrobial products 10, 100 may surround, may enclose, may cover and/or may separate one or more first food products and/or one or more second food products. As a result, the antimicrobial products 10, 100 may prevent and/or may delay the micro-organism from contaminating one or more first food products and/or one or more second food products during wrapping, packaging, shipping, transporting and/or delivering one or more first food products and/or one or more second food products.

The antimicrobial products 10, 100 may have the base layer 12 having the top side 14 and/or the bottom side 16. The first water resistant layer 18 may be connected to, may attached to, may be adhered to and/or may cover the top side 12 of the base layer 12. The first antimicrobial layer 22 may be connected to, may be attached to, may be adhered to and/or may cover the first water resistant layer 18. The second water resistant layer 20 may be connected to, may be attached to, may be adhered to and/or may cover the bottom side 16 of the base layer 12. The second antimicrobial layer 102 may be connected to, may be attached to, may be adhered to and/or may cover the second water resistant layer 20. The first color and/or the second color of the base layer 12 and/or the first water resistant layer 18, respectively, may be exposed and/or may be displayed via the second water resistant layer 20 and the second antimicrobial layer 102 and/or the first antimicrobial layer 22, respectively. The first color and/or the second color may enhance and/or may improve the appearance and/or the color of the first food product and/or the second food product, respectively. The antimicrobial products 10, 100 may be formed to provide a texture having the first depressions 24 and/or the second depressions 26 for contacting and/or for abutting the first food product and/or the second food product.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. An antimicrobial product for preventing contamination of a first food product or a second food product by a micro-organism wherein the first food product has a first color wherein the second food product has a second color, the antimicrobial product comprising:
   a base layer defined by a length and a width wherein the base layer has a top side and a bottom side wherein the bottom side is located opposite to the top side and further wherein the base layer forms a plane;
   a first antimicrobial layer connected to the top side of the base layer wherein the first antimicrobial layer covers the top side of the base layer;
   a second antimicrobial layer connected to the bottom side of the base layer wherein the second antimicrobial layer covers the bottom side of the base layer wherein the first antimicrobial layer or the second antimicrobial layer prevents migration of the micro-organism across the plane of the base layer and further wherein at least one of the first antimicrobial layer and the second antimicrobial layer is transparent; and
   a plurality of depressions formed in the base layer, wherein the plurality of depressions are uniform and are continuous on the base layer, wherein the first antimicrobial layer or the second antimicrobial layer prevents the micro-organism from contaminating the first food product wherein each of the plurality of depressions has a square shape and further wherein each of the plurality of depressions has the same shape.

2. The antimicrobial product of claim 1 further comprising:
   a water resistant layer attached to the top side of the base layer wherein the water resistant layer is located between the base layer and the first antimicrobial layer.

3. The antimicrobial product of claim 1 further comprising:
   a water resistant layer attached to the bottom side of the base layer wherein the water resistant layer is located between the base layer and the second antimicrobial layer and further wherein the water resistant layer is transparent.

4. The antimicrobial product of claim 1 further comprising:
   a first color displayed by the top side of the base layer wherein the first color corresponds to the first color of the first food product and further wherein a second color is displayed by the bottom side of the base layer and corresponds to the second color of the second food product.

5. The antimicrobial product of claim 1 further comprising:
   silver zeolite located within the antimicrobial layer.

6. The antimicrobial product of claim 1 wherein at least one of the first antimicrobial layer and the second antimicrobial layer is a coating containing silver zeolite.

7. The antimicrobial product of claim 1 wherein at least one of the first antimicrobial layer and the second antimicrobial layer is a layer of polyethylene covered with silver zeolite.

8. An antimicrobial product for preventing contamination of a first food product or a second food product from a micro-organism wherein the first food product has a first color wherein the second food product has a second color, the antimicrobial product comprising:
   a base layer defined by a length and a width wherein the base layer has a top side and a bottom side wherein the bottom side is opposite to the top side and further wherein the base layer forms a plane wherein a first color is associated with the bottom side of the base layer wherein the first color of the bottom side corresponds to the first color of the food product;
   a water resistant layer attached to the bottom side of the base layer wherein the water resistant layer is transparent; and
   a first antimicrobial layer connected to the top side of the base layer wherein the first antimicrobial layer covers the top side of the base layer wherein the first antimicrobial layer prevents the micro-organism from contaminating the first food product or the second food product.

9. The antimicrobial product of claim 8 further comprising:
   an additional water resistant layer attached to the top side of the base layer wherein the water resistant layer is located between the first antimicrobial layer and the base layer and further wherein the additional water resistant layer has a second color which corresponds to the second color of the second food product wherein the first antimicrobial layer is transparent.

10. The antimicrobial product of claim 8 further comprising:
- a second antimicrobial layer connected to the bottom side of the base layer wherein the second antimicrobial layer prevents the micro-organism from contaminating the first food product or the second food product and further wherein the second antimicrobial layer is transparent.

11. The antimicrobial product of claim 8 wherein the first antimicrobial layer is transparent and further wherein the top side of the base layer has a second color which corresponds to the second color of the second food product.

12. The antimicrobial product of claim 8 further comprising:
- a plurality of depressions formed in the base layer and the first antimicrobial layer wherein each of the plurality of depressions has a square shape and further wherein each of the plurality of depressions has the same shape.

13. A method for using an antimicrobial product to prevent contamination of a first food product or a second food product by a micro-organism wherein the first food product has a first food product color wherein the second food product has a second food product color, the method comprising the steps of:
- providing a base layer defined by a length and a width wherein the base layer has a top side and a bottom side wherein the bottom side is located opposite to the top side;
- coloring the bottom side of the base layer to have a first color wherein the first color is based on the first food product color;
- attaching a water resistant layer to the top side of the base layer;
- coloring the water resistant layer to have a second color wherein the first color is a different color than the second color and further wherein the second color is based on the second food product color;
- attaching a first antimicrobial layer to the water resistant layer wherein the first antimicrobial layer prevents the micro-organism from contaminating the first food product or the second food product and further wherein the first antimicrobial layer is transparent; and
- forming a texture on the antimicrobial product wherein the texture has a plurality of depressions and further wherein each of the plurality of depressions has a square shape and each of the plurality of depressions has the same shape.

14. The method of claim 13 further comprising the step of:
- positioning the first food product on the bottom side of the base layer.

15. The method of claim 13 further comprising the step of:
- positioning the second food product on the first antimicrobial layer.

16. The method of claim 13 further comprising the step of:
- enclosing the first food product or the second food product with the antimicrobial product wherein the antimicrobial product prevents the micro-organism from contaminating the first food product or the second food product.

17. The method of claim 13 further comprising the step of:
- inserting the antimicrobial product between the first food product and the second food product wherein the first color is adjacent to the first food product and further wherein the second color is adjacent to the second food product.

18. The method of claim 13 further comprising the step of:
- providing air flow to the first food product or the second food product via the texture of the antimicrobial product.

19. The method of claim 13 further comprising the step of:
- connecting a second antimicrobial layer to the bottom side of the base layer of the antimicrobial product wherein the second antimicrobial layer prevents the micro-organism from contaminating the first food product or the second food product and further wherein the second antimicrobial layer is transparent.

20. The method of claim 13 wherein each of the plurality of depressions has the same shape.

* * * * *